United States Patent [19]
Patashnick et al.

[11] Patent Number: 5,279,970
[45] Date of Patent: * Jan. 18, 1994

[54] CARBON PARTICULATE MONITOR WITH PRESEPARATOR

[75] Inventors: Harvey Patashnick; Georg Rupprecht, both of Voorheesville, N.Y.

[73] Assignee: Rupprecht & Patashnick Company, Inc., Albany, N.Y.

[*] Notice: The portion of the term of this patent subsequent to May 5, 2009 has been disclaimed.

[21] Appl. No.: 962,695

[22] Filed: Oct. 19, 1992

Related U.S. Application Data

[60] Division of Ser. No. 877,542, May 1, 1992, Pat. No. 5,196,170, which is a continuation-in-part of Ser. No. 612,562, Nov. 13, 1990, Pat. No. 5,110,747.

[51] Int. Cl.$^5$ .................... G01N 15/00; G01N 21/76
[52] U.S. Cl. .................... 436/133; 436/145; 436/157; 436/160; 436/177; 422/83; 422/101; 73/23.33; 73/28.01; 73/28.04; 73/28.05; 73/31.07; 110/217
[58] Field of Search .................. 422/83, 101; 436/133, 436/145, 157, 160, 177; 73/23.33, 28.01, 28.04, 28.05, 31.07; 110/217

[56] References Cited

U.S. PATENT DOCUMENTS

| | | | |
|---|---|---|---|
| 3,985,505 | 10/1976 | Bredeweg | 23/230 PC |
| 5,110,747 | 5/1992 | Patashnick | 436/133 |

FOREIGN PATENT DOCUMENTS

| | | | |
|---|---|---|---|
| 3009861 | 1/1988 | Japan | 436/133 |

OTHER PUBLICATIONS

Ohta, S. et al. "Measurement of Particulate Carbon in Urban and Marine Air in Japanese Areas", ATMOS Environment, vol. 18 No. 11 1984.

Cadle, S. H. "Automated Carbon Analyzer for Particulate Samples"Anal. Chem. 1980. 52, 2202-2206.

Primary Examiner—James C. Housel
Assistant Examiner—David Redding
Attorney, Agent, or Firm—Heslin & Rothenberg

[57] ABSTRACT

Carbon particulate concentration of diesel exhaust or other sampled gas is measured by collecting the particulate on a high efficiency filter while measuring the amount of sampled gas passing through the filter. The filtered particulate is then heated in an oxygen rich environment to oxidize carbon within the particulate to carbon dioxide. The amount of resulting carbon dioxide is measured with a closed measurement loop to derive a corresponding measurement of the amount of filtered particulate. Particulate concentration is calculated by comparing the amount of carbon particulate with the measured amount of sampled gas passed through the filter. Filtered particulate can be heated incrementally to obtain a measurement of volatile carbon components within the particulate prior to the oxidation of the non-volatile carbon component. The filter employed to collect the carbon particulate is of a high temperature resistant type making it reusable and can be either integral with or inserted into the oxidation chamber of the instrument. Oxidation of the particulate inherently concurrently cleans the filter for reuse. An upstream preseparator can extend the life of the high efficiency filter. Particulate can also be collected for analysis by using an accelerating impaction nozzle in conjunction with a heatable impaction plate.

21 Claims, 6 Drawing Sheets

CARBON PARTICULATE MONITOR WITH PRESEPARATOR

This application is a division of application Ser. No. 07/877,542, filed May 1, 1992, now U.S. Pat. No. 5,196,170 which is a continuation-in-part of application Ser. No. 07/612,562, filed Nov. 13, 1990, now U.S. Pat. No. 5,110,747.

BACKGROUND OF THE INVENTION

The present invention relates generally to measurement of carbon particulates, and more particularly to a method and apparatus for determining the particulate level or concentration of a sampled gas, e.g. diesel exhaust.

The quality of air has become an important environmental concern within recent years. In an effort to curb air pollution and maintain air quality, strict vehicle exhaust emission guidelines have been set by federal and state authorities. Requirements for diesel emissions are extremely stringent because of the harmful effects of diesel exhausts within the atmosphere. Therefore, each diesel vehicle sold, for example within the United States, must pass certain emission tests and meet strict environmental emission standards. To determine if emission standards have been met, it is necessary to measure the particulate concentration of diesel exhaust. In order to accurately determine whether a diesel engine meets emission standards, a reliable reading of the particulate concentration of diesel exhaust is necessary. An inaccurate reading of diesel particulate concentration could result in a diesel engine improperly passing or failing emission tests. It is, therefore, desirable to utilize a technique for accurately and reliably measuring the particulate concentration of diesel exhaust.

Presently, diesel particulate is measured using a few different types of systems. One particular technique involves a direct measurement of the mass of particulate within exhaust on a real-time basis. With this technique a tapered element oscillating microbalance such as that shown in U.S. Pat. No. 4,391,338 is capable of measuring the mass of particulate deposited on a filter. This technique is not inexpensive and generally requires a dilution tunnel for proper use. Another technique for measuring the amount of particulate concentration of diesel exhaust involves optical measurements. This technique, however, suffers from a lack of accuracy and does not provide consistently reliable measurements of particulate mass. Another technique for measuring the particulate concentration of diesel exhaust involves forcing a measured amount of exhaust through a filter which collects the particulate therein, and then weighing the filter. The filter is preconditioned and pre-weighed so that the difference in weight of the filter before and after its use is representative of the amount of particulate within the exhaust. The disadvantage with this particular system is that it is extremely time consuming and labor intensive. Furthermore, the filter is not reusable after each measurement cycle thereby making it necessary to obtain a new filter for each diesel particulate measurement.

It is therefore an object of the present invention to provide a technique to accurately measure the particulate concentration of diesel exhaust.

It is also an object of the present invention to provide a technique for measuring the particulate concentration of diesel exhaust which is not labor intensive or time consuming.

It is also an object of the present invention to provide a technique for measuring the particulate concentration of diesel exhaust which utilizes a reusable filter or particulate collector to avoid the necessity of disposing of filters or collectors after they have been used to collect particulate.

It is also an object of the present invention to provide a technique for measuring the particulate concentration of diesel exhaust which provides consistently reliable readings.

It is also an object of the present invention to provide a technique to measure the concentration of non-volatile diesel particulate and/or volatile diesel particulate.

It is a further object of the present invention to provide a technique for measuring the carbon particulate level or concentration not only of diesel exhaust but also of other gaseous mixtures and samples.

SUMMARY OF THE INVENTION

The shortcomings of the prior art are overcome and the objects of the present invention are achieved, by utilizing a technique for measuring carbon particulate concentration of diesel exhaust or other sampled gas in accordance with the present invention. The invention involves a method for determining the carbon particulate concentration of diesel exhaust or other sampled gas which includes filtering diesel exhaust or other sampled gas to separate and collect carbon particulate on a high efficiency filter, measuring the amount of exhaust or sampled gas filtered, exposing the filtered particulate to oxygen, heating the filtered particulate to oxidize carbon and form carbon dioxide, measuring the level of the resultant carbon dioxide to arrive at a level of carbon therein, and calculating the particulate concentration by comparing the level of carbon with the amount of exhaust or sampled gas measured.

The method may also include removing residual carbon dioxide gas from within the oxidizing environment prior to oxidation. The method may also include heating the filtered particulate incrementally to eliminate volatile components within the particulate prior to oxidation of the non-volatile carbon, and may further comprise calculating the volatile and/or non-volatile carbon particulate components.

In a further aspect, the invention involves apparatus for determining the carbon particulate level or concentration of diesel exhaust or other sampled gas. The apparatus comprises a means for containing a filter for collecting carbon particulate from diesel exhaust or other sampled gas, means for removing residual carbon dioxide from within the means for receiving the filter, means for supplying oxygen within the means for receiving the filter, means for heating the filter to oxidize carbon collected by the filter, and means for measuring the amount of carbon dioxide produced from the oxidation of carbon. The apparatus may also comprise a filter for collecting carbon particulate from diesel exhaust or other sampled gas and a means for measuring the amount of diesel exhaust or other sampled gas directed through the filter. The apparatus may further comprise a means for heating the filter incrementally to separate volatile from non-volatile components of the filtered particulate. The apparatus may also include means to oxidize such volatile particulate components to facilitate a separate measurement of the volatile carbon components, and means for converting any CO produced by partial oxidation into $CO_2$.

A means for directing diesel exhaust through the filter may be included which comprises a diesel exhaust inlet mountable in fluid flow relationship between the filter and an exhaust pipe of the diesel engine. The means for supplying oxygen may comprise a valve means capable of directing air or other oxygen containing gas into the means for receiving the filter. The apparatus may further comprise valve means for preventing gas exiting the means for receiving a filter from entering the means for measuring the carbon dioxide or the means for measuring the amount of diesel exhaust or other sampled gas directed through the filter, and a valve means for preventing diesel exhaust or other sampled gas from flowing through the filter. The apparatus may further comprise a piping system interconnecting the means for receiving the filter, the means for oxidizing volatile particulate components, and the means for measuring the amount of carbon dioxide produced from the oxidation of carbon, in a closed loop. Pump means, pressure regulator means and/or flow regulator means may advantageously be incorporated in the closed loop. A section of the piping system connecting the means for containing the filter and the means for oxidizing volatile particulate components is preferably heated to prevent volatile components from condensing therein. The filter is preferably high temperature resistant to allow reuse and may be comprised of either a ceramic type trap or quartz fiber filter. The means for measuring the carbon dioxide may comprise an infrared absorption analyzer. The means for measuring the amount of filtered diesel exhaust or other sampled gas may comprise a flowmeter, or a flow controller.

The filter may be built into the apparatus and the whole apparatus connected to an exhaust pipe or outlet of a diesel engine or vehicle under test. Alternatively, a separate sampling unit containing the filter and a means for measuring the amount of diesel gas passing through the filter can be connected to the exhaust pipe. After sampling, the particulate laden filter can be removed from the sampling unit and placed in a separate structure for oxidation of the particulate and measurement of resulting carbon dioxide.

In another aspect of the invention, the operation of the apparatus can be automated and a microcomputer or the like can be used to calculate the particulate concentration from the measurements of $CO_2$ and filtered diesel exhaust or other sampled gas.

In a further aspect of the invention, the amount of different species of volatile particulate components may be determined by correlating $CO_2$ measurements with filter heating temperatures.

According to another aspect of the invention, rather than using a filter, carbon particulate can be collected by passing the diesel exhaust or other sampled gas through an accelerating impaction nozzle and impacting carbon particulate on a heatable impaction plate.

In yet another aspect of the present invention, a preseparator can be located upstream of the filter or other fine particulate collector to remove particulate from the gas stream and/or capture larger size particulate and thereby reduce clogging and extend the useful life of the filter or other fine particulate collector. The preseparator may include a heater to facilitate oxidation, measurement and thermal analysis of carbon particulate captured therein.

BRIEF DESCRIPTION OF THE DRAWINGS

These and other objects, features, aspects and advantages of the present invention will be readily understood from the following detailed description, when read in conjunction with the accompanying drawings, in which:

FIG. 3A illustrates further details of the impaction chamber equipment of FIG. 3;

In the drawings, like reference numbers are used to identify like parts.

DETAILED DESCRIPTION

Figure 1:
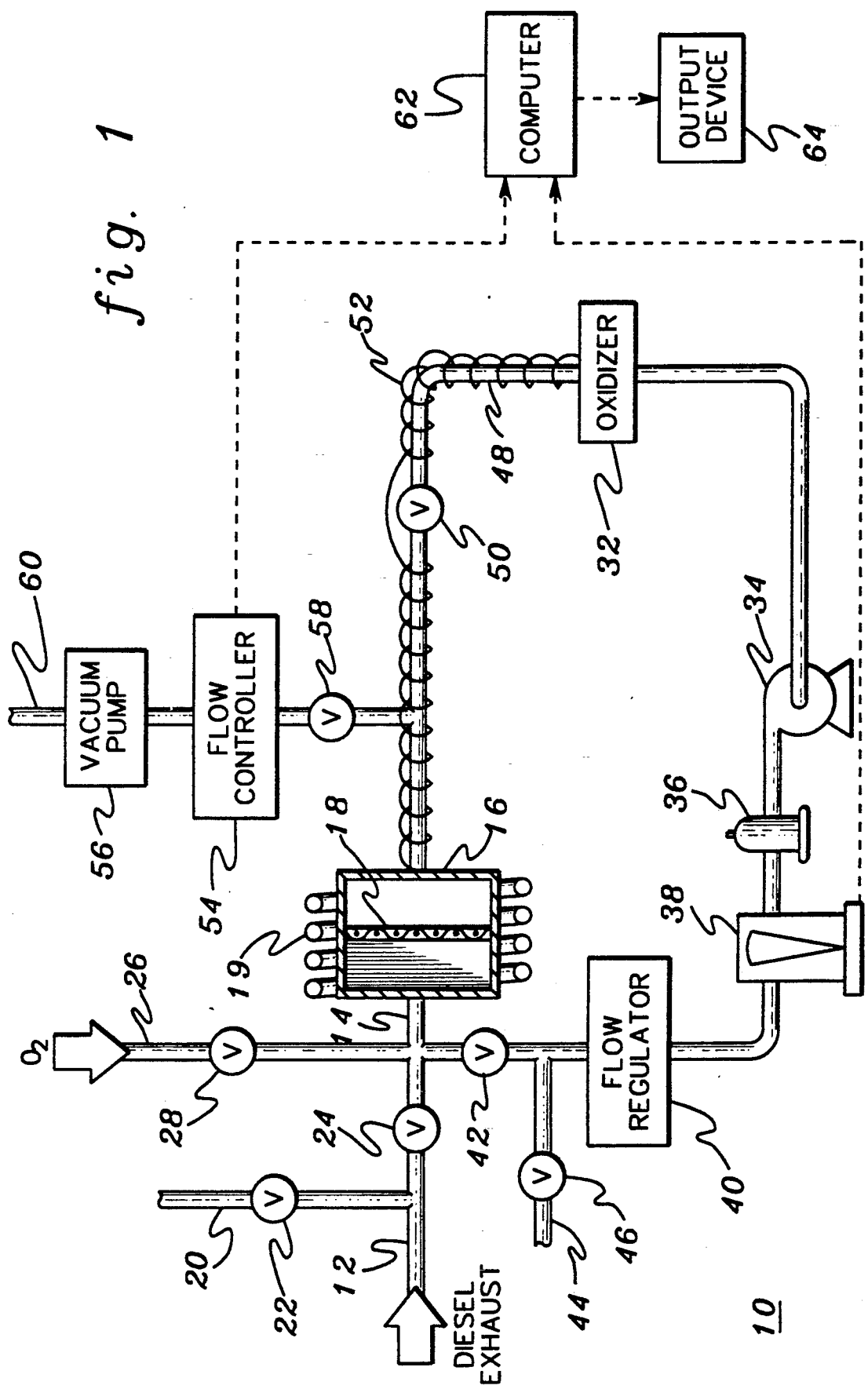
FIG. 1 depicts a first embodiment of the apparatus of the present invention employing a high efficiency filter and useful in sampling and in measuring the particulate concentration of diesel exhaust or other sampled gas.

A first embodiment of apparatus for determining the particulate concentration of diesel exhaust, in accordance with the principles of the present invention, is shown in FIG. 1. The nature, function and interconnection of the components of the system will now be described, followed by a full description of the operation of the apparatus.

The apparatus 10 contains an inlet 12 which may be connected to the outlet end of an exhaust pipe of a diesel engine or diesel powered vehicle (not shown) thereby enabling the exhaust to flow through the inlet 12 and into the particulate concentration measuring system. The inlet 12 may be attached directly to the diesel exhaust pipe, or a flexible tubing or duct may be used to place inlet 12 in fluid flow relationship with the diesel exhaust pipe.

The inlet 12 is connected by a conduit passageway 14 to a chamber 16 capable of holding a filter 18 therein. A discharge nipple 20 with a valve 22 therein is located at a point between the inlet 12 and chamber 16. When the valve 22 is opened, diesel exhaust which flows through the inlet 12 will be allowed to flow through the discharge nipple 20 and out of the system. A valve 24 is located in the passageway 14 at a point downstream from the valve 22. When the valve 24 is opened, exhaust is allowed to flow towards the chamber 16. When the valve 24 is closed, however, exhaust is prevented from flowing towards the chamber 16 and any gas within the chamber 16 is prevented from flowing towards the valve 22 or inlet 12. A supply tube or nipple 26 is connected to the passageway 14 downstream from the valve 24 and upstream from the chamber 16. The supply nipple 26 has a valve 28 connected thereto and is connected to an oxygen rich purge gas supply. When the valve 28 is opened and the valve 24 is closed, oxygen rich purge gas is allowed to flow into and within the chamber 16.

The filter chamber 16 contains a filter 18 which is capable of filtering diesel particulate from diesel exhaust with high efficiency (hereinafter sometimes referred to as a fine particulate filter or a high efficiency filter). Preferably, a high temperature resistant filter, such as a quartz fiber, or ceramic trap type, is employed, allowing for filter reuse. The filter 18 is mounted within the chamber 16 in such a fashion as to prevent exhaust gases from flowing through the chamber without flowing through the filter 18. A means for heating the chamber is contained within the system. The heating means may be in the form of a heating coil 19 surrounding the chamber 16 or alternatively may comprise a heating element or heating coil (not shown) within the chamber 16.

Chamber 16 is connected via a piping system 30 in fluid flow relationship and in a closed loop configuration with a series arrangement of oxidizer 32, pump 34, pressure regulator 36, carbon dioxide meter 38, flow regulator 40 and valve 42. During a measurement cycle, gases exiting chamber 16 are continuously circulated through this closed loop configuration.

Oxidizer 32 may comprise a simple heater such as a glowing nichrome wire, or heated platinum or nickel tubing, or may be a conventional catalytic converter available in the automotive industry. Oxidizer 32 can be advantageously employed to oxidize volatile particulate components, as well as to convert into carbon dioxide any carbon monoxide produced in chamber 16. These functions are more fully described hereinafter.

Pump 34 located downstream from oxidizer 32 serves to pump gases through the piping system 30. Pump 34 is preferably a unidirectional, internally sealed, closed circuit pump.

Gases output from pump 34 flow through pressure regulator 36 into $CO_2$ meter 38. Meter 38 can take many different forms but preferably is of an infrared absorption analyzer type. Such analyzers are commercially available in industrially hardened form. Pressure regulator 36 serves to reduce the pressure of gases entering meter 38 to a standard, e.g. ambient level, in order to maintain a constant pressure in $CO_2$ meter 38 and thereby avoid false indications due to pressure changes.

Flow regulator 40 is employed to maintain a constant flow through the closed loop configuration. Valve 42 serves to either permit or preclude fluid flow between regulator 40 and conduit 14 leading to chamber 16. An outlet pipe 44 is connected via valve 46 to piping system 30 between regulator 40 and valve 42.

The section 48 of piping system 30 connecting chamber 16 to oxidizer 32 includes a valve 50 and is surrounded by a heating coil 52 or other heating means. Valve 50 serves to control the flow of gases into oxidizer 32 while heater 52 is used to prevent volatile particulate components from condensing within pipe section 48.

A flow controller 54 and an associated vacuum pump 56 are connected via valve 58 to pipe section 48 at a point intermediate of chamber 16 and valve 50. Vacuum pump 56 serves to draw diesel exhaust through filter 18 in chamber 16 while flow controller 54 provides a measure of the amount of filtered diesel exhaust. Valve 58 provides a means for controlling flow through controller 54 and vacuum pump 56 to an outlet pipe 60. Instead of flow controller 54 and vacuum pump 56 a conventional flow meter can be used to measure the amount of diesel exhaust passing through filter 18. The pressure differential supplied by the diesel exhaust coming out of the engine may be used to drive the flow through chamber 16 and the flow meter.

An electrical signal representative of the amount of filtered diesel exhaust can be provided by flow controller 54 (or an equivalent flow meter) to a computer 62. Computer 62 also receives an electrical signal representative of the amount of carbon dioxide measured by meter 38. Computer 62 which can be a microprocessor or PC type computer determines, from these readings, the particulate concentration of the diesel exhaust. The particulate concentration can be displayed by an output device 64 connected to computer 62. Output device 64 may comprise, for example, a printer, meter or display device. Computer 62 can also be programmed in conventional fashion to control the operation of the valves, heating means and other components of the system in accordance with a desired schedule.

The system 10 operates to measure the particulate concentration of diesel exhaust by trapping diesel exhaust particulate within the filter 18 and measuring the volume of the exhaust which flows therethrough. After a sufficient amount of exhaust is filtered, oxygen rich gas is forced into the filter chamber 16 to drive out any exhaust fumes therein and provide an oxygen rich environment. The oxygen rich gas is also used to purge the closed loop measurement subsystem and to equalize the environment therein. The heating means is then activated to raise the temperature within the filter chamber to a sufficient level so that particulate trapped in filter 18, which particulate is nearly 100% carbon, oxidizes to carbon dioxide. Depending upon the temperature function used to heat the filter chamber, volatile particulate components may be driven off the filter without being oxidized. Oxidizer 32 serves to oxidize such volatile components as well as to convert any partially oxidized carbon in the form of carbon monoxide into carbon dioxide. The carbon dioxide is then measured by the carbon dioxide meter 38 to arrive at a carbon level. Since the particulate within the exhaust is nearly 100% carbon, a measurement of the amount of carbon within the exhaust yields the amount of particulate. The amount of exhaust measured to have flowed through the filter 18 is compared to the amount of particulate to arrive at a particulate concentration level. Oxidation of particulate trapped in the filter also serves to clean the filter sufficiently to allow it to be reused again in the same system. Therefore, there is no need to independently clean or to dispose of the filter after each sampling.

The system is used to measure the particulate concentration of diesel exhaust by attaching the inlet 12 to an exhaust pipe of a diesel powered vehicle so that the exhaust flows within the inlet 12. If the diesel engine is operating, the valve 22 should be opened and all other valves within the system closed so that the exhaust flows through valve 22 out of the system. To begin a sampling cycle, valve 24 and valve 58 are opened to allow exhaust to flow through the chamber 16 and filter 18, as well as through the flow controller 54, vacuum pump 56 and the outlet 60 of the system. Valve 22 may be closed completely, or partially if the filter is not capable of handling high exhaust capacity. As the exhaust flows through the filter 18, diesel particulate will be collected within the filter while the flow through the filter is measured using flow controller 54 or other suitable flowmeter.

After a predetermined period of time (or a predetermined volume or mass of exhaust flow through the system), the valve 24 can be closed and valve 22 opened to prevent exhaust from flowing through the filter and forcing exhaust to flow out the discharge nipple 20. Valve 28 is then opened to allow oxygen rich gas to flow into the chamber 16 and to force any residual carbon dioxide within chamber 16 out of the system through outlet pipe 60. After an appropriate period of time, valve 58 is closed and valves 50 and 46 are opened to purge the rest of the system (i.e. oxidizer 32, pump 34, pressure regulator 36, meter 38, flow regulator 40 and the interconnecting piping system 30) of any $CO_2$ left from the previous measurement cycle. The purged $CO_2$ leaves the system through outlet pipe 44. This last step also serves to equalize the environment in the filter chamber 16 and meter 38.

The oxygen rich gas connected to the supply nipple 26 and used to purge the system may be air or some other gaseous mixture containing a small percent of carbon dioxide in which case the purging process establishes a common background level of $CO_2$ in the closed loop of the system which can be measured by meter 38 and subtracted from subsequent reading to calculate the amount of diesel particulate. When measuring very minute amounts of diesel particulate it may be advantageous to use a $CO_2$-free gas for purging, such as pure oxygen or a mixture of oxygen and nitrogen. In this case, all $CO_2$ measured by meter 38 will be the result of oxidation of particulate.

After a sufficient period of time, any exhaust gas within the system will have been purged therefrom and the chamber 16 will be completely filled with oxygen rich gas. Valves 46 and 28 can then be closed and valve 42 opened to isolate the closed loop and prevent any gases circulating therein from escaping. The heater 19 can then be turned on to facilitate oxidation of the carbon within the filter 18.

In one mode of operation, the particulate on filter 18 can be rapidly subjected to a high temperature on the order of 700° C. to quickly burn off all of the particulate, both volatile hydrocarbon components and non-volatile carbon components. Oxidizer 32 ensures that all of the carbon in the particulate is converted into $CO_2$. The carbon dioxide meter 38 measures the resulting amount of carbon dioxide which is directly related to the amount of carbon oxidized. The amount or level of diesel particulate within the exhaust is substantially equal to the amount of carbon.

By comparing this amount of diesel particulate with the amount of exhaust measured by flow controller 54, particulate concentration can be determined. Computer 62, is connected to flow controller 54 and to carbon dioxide meter 38 and receives measurement readings therefrom. The output of meter 38 is a measurement of the parts per million of $CO_2$ in the recirculating gas stream within the closed measurement loop. Knowledge of the volume of the loop (gained through direct measurement or prior calibration by injection of known amounts of $CO_2$ into the loop) allows ready calculation of the number of molecules of $CO_2$ by the computer. Each molecule of $CO_2$ corresponds to an individual atom of carbon caught in the filter. From the number of carbon atoms, the mass of the carbon can be calculated in known fashion. The mass of the carbon is for all practical purposes equal to the mass of the particulate.

Dividing the mass of the particulate by the measured amount of filtered diesel exhaust provides an accurate measure of particulate concentration. The computer can thus calculate the particulate concentration of the diesel exhaust from the measurement readings and provide an output signal representative of particulate concentration to an output device 64, e.g. a printer, meter or display device. Computer 62 can also advantageously be employed to control the operation of the valves, heating means and other components of the system in accordance with a desired schedule.

Since the diesel particulate is effectively 100% carbon, complete oxidation of the carbon within the filter cleans the filter entirely and allows it to be reused in the same system to again trap diesel particulate for oxidation into carbon dioxide. Accordingly, high efficiency filters which are also high temperature resistant can be effectively reused.

Figure 2:
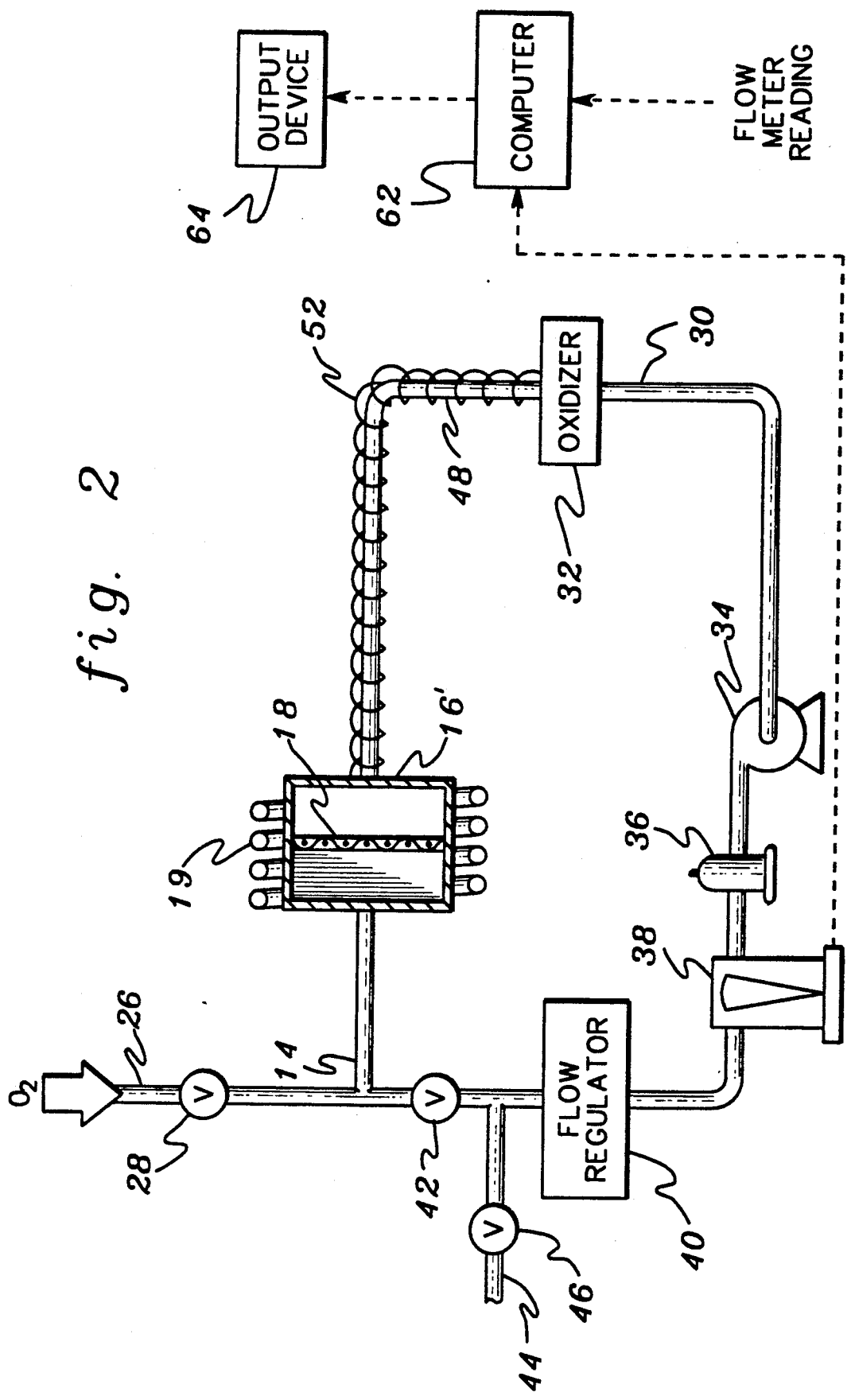
FIG. 2 illustrates another embodiment of the apparatus of the present invention for receiving a particulate laden filter and measuring particulate concentration of diesel exhaust or other sampled gas.

In an alternative embodiment of the system of the present invention, the exhaust particulate can be trapped within the high efficiency filter prior to the filter being placed into a chamber for oxidation. In such a system, exhaust does not have to flow into the system and the measurement apparatus need not be connected to a diesel exhaust pipe. The alternative embodiment, shown in FIG. 2, contains a conduit 26 connecting the chamber 16' to an oxygen rich gas supply and a valve 28 to allow the oxygen rich gas to flow into the chamber 16'. Chamber 16' is constructed to allow ready insertion of a particulate laden filter 18 therein.

The filter 18, is first placed within a separate sampling unit (not shown) for allowing exhaust to flow therethrough. In this embodiment, the sampling unit is connected to the exhaust pipe of a diesel engine vehicle and diesel particulate is trapped within the filter while the flow therethrough is being measured. After filtering a sufficient amount of particulate from the exhaust, the filter 18 can then be removed from the sampling unit and placed within the chamber 16'. The system is then used as previously described in the aforementioned embodiment. The valve 28 upstream of the chamber can be opened allowing the oxygen rich gas to enter chamber 16' therethrough and valve 46 can be opened while valve 42 remains closed in order to purge the measurement loop. Valves 46 and 28 are then closed and valve 42 opened to establish the closed loop recirculating gas stream. The means for heating the filter can then be activated to facilitate oxidation of the carbon in filter 18 into carbon dioxide. The carbon dioxide meter 38 determines the amount of carbon dioxide within the system. The output of $CO_2$ meter 38 and a flowmeter reading representative of the amount of filtered diesel exhaust are processed by computer 62 to determine the particulate concentration of the exhaust.

In a further aspect of the invention applicable to both of the previously described embodiments, volatile hydrocarbon components can be separated from the non-volatile carbon components of the particulate trapped in the filter. In this refinement, the filter with particulate trapped therein is heated imcrementally (e.g. with a ramp function or in stages) in order to first drive off volatile components which can be oxidized into $CO_2$ by oxidizer 32 and measured by meter 38 and analyzed separately before the non-volatile carbon is oxidized.

Figure 4:
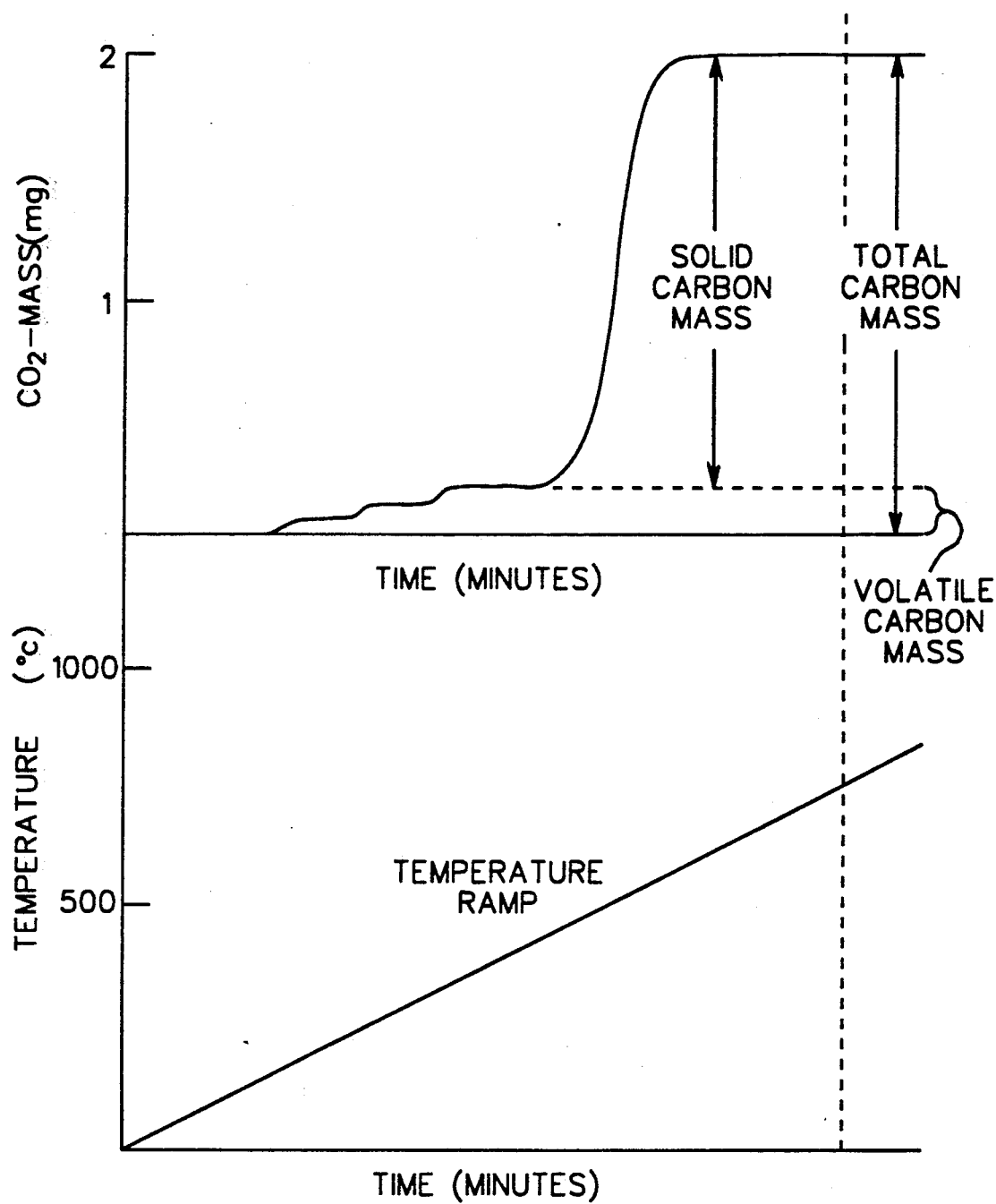
FIG. 4 presents an illustrative particulate heating temperature function and a corresponding $CO_2$ mass measurement profile useful in explaining how volatile and non-volatile particulate components can be measured.

As schematically illustrated in FIG. 4, the filter chamber can be heated along a temperature ramp at a particular rate; the rate depending in part upon the heat capacity of the filter chamber. As the heat gradually increases, volatile hydrocarbon components of the particulate evaporate off of the filter, without being oxidized in the filter chamber, and enter the circulating gas stream. Oxidizer 32 oxidizes the volatile components converting them to $CO_2$ which is measured by meter 38. As shown in the upper portion of FIG. 4, as the temperature in the filter chamber gradually increases other hydrocarbons are released from the filter, oxidized by oxidizer 32, and the resulting $CO_2$ measured by meter 38. Longer chain hydrocarbons have a lower vapor pressure and therefore evaporate later, i.e. at a higher temperature. Accordingly, as the temperature is gradually increased, there is a natural discrimination with respect to which species of hydrocarbons are released. The corresponding $CO_2$ measurements can therefore be used to provide insight into characterizing the amounts of various hydrocarbon constituents of the exhaust.

In the thermal analysis example illustrated, virtually all of the volatile particulate constituents have been driven off by the time the temperature reaches about 400° C. Heating beyond this temperature causes the non-volatile carbon to oxidize resulting in a substantial increase in measured $CO_2$. In the range of 700°–800° C., all of the carbon has been burnt off.

The section of piping between the filter chamber and oxidizer 32 is preferably heated to prevent any condensation of volatile hydrocarbons within this piping section.

Referring again to the $CO_2$ profile of FIG. 4, the top level provides a measure of the total carbon mass, both volatile and non-volatile, in the sample. The reading before the final plateau indicates the amount of volatile carbon components. The difference between the highest reading and the volatile carbon reading provides a measure of the mass of the non-volatile carbon. In this fashion, a measure of volatile to non-volatile components of the diesel particulate can be achieved.

Alternatively, two samples could be taken where one is totally oxidized and the other is heated first to drive off volatile components without oxidation and then the residue heated and oxidized. The latter sample yields a measurement of the non-volatile component which can be subtracted from the measurement of total sample to yield the amount of the volatile components.

Figure 3:
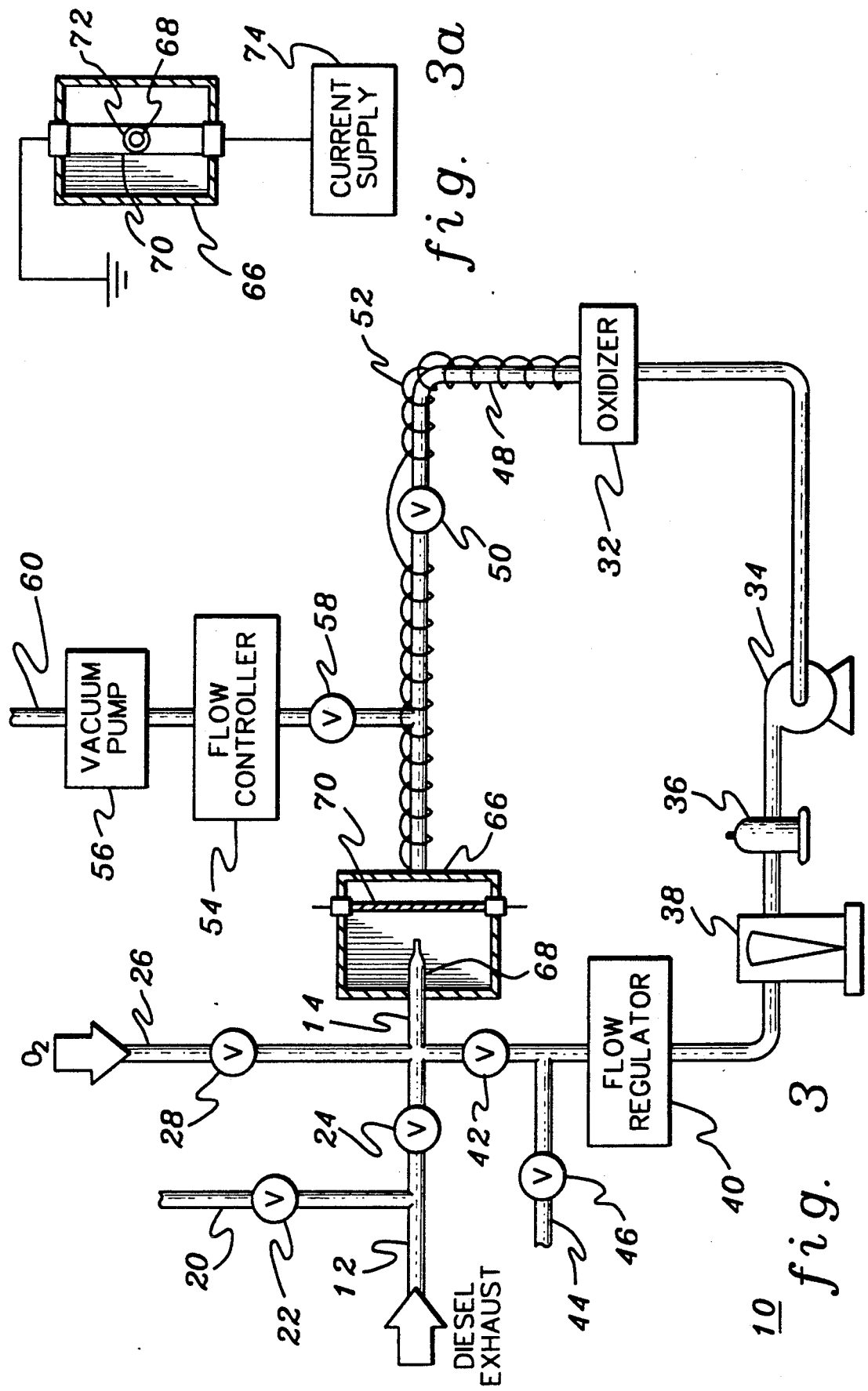
FIG. 3 illustrates an embodiment of the present invention employing an impaction nozzle and a heatable impaction plate within an impaction chamber used to collect carbon particulate.

FIGS. 3 and 3A depict an embodiment of the invention in which particulate is collected by impaction from a nozzle onto a heatable impaction plate, rather than with a filter. The system is identical to that previously described, except that the filter chamber and filter are replaced by an impaction chamber 66 containing an impaction nozzle 68 and a heatable impaction plate 70. In operation, the diesel exhaust is directed through acceleration nozzle 68 so that the particulate is impacted against and sticks to the heatable impaction plate 70. The particulate deposits in an impaction area 72 on the plate while the flow of exhaust gas continues around the plate and then out of the impaction chamber. Impaction plate 70 may comprise a small temperature controlled hot plate or a band of material through which a current can be run from a current supply 74 to cause the band to heat up. Once the particulate has been deposited on impaction plate 70, the measurement process is identical to that described earlier. One advantage of the impaction plate approach is that it allows the deposited particulate to be heated more directly than with a filter chamber. As in the filter examples, the deposited particulate is totally consumed upon oxidation allowing the impaction plate to be reused for future measurement cycles.

While direct monitoring of raw diesel exhaust is useful for engine testing, the method and apparatus of the present invention can be used in other situations as well. These include applications in which the diesel exhaust is diluted and/or mixed with other particulates (carbonaceous and/or inorganic), as well as for monitoring of gas-borne carbon particulates of a non-diesel origin. Such applications include the monitoring of carbon (soot) particulates (diesel or otherwise) in ambient air, along highways, or in the workplace. In these examples, diesel particulates are usually of particular concern and they are present along with inorganic particulates.

Using the previously described collecting and analyzing apparatus of the present invention, all carbon particulates (diesel or otherwise) from a sampled gas can be detected. However, when the high efficiency filter or collector of the present invention is used to trap all particulates including non-burnable inorganic ones, the filter renewal capability may be impaired in that the inorganic particulates will remain trapped in the filter (or equivalent collector) and may eventually cause it to clog, thus limiting its useful life.

Figure 5:
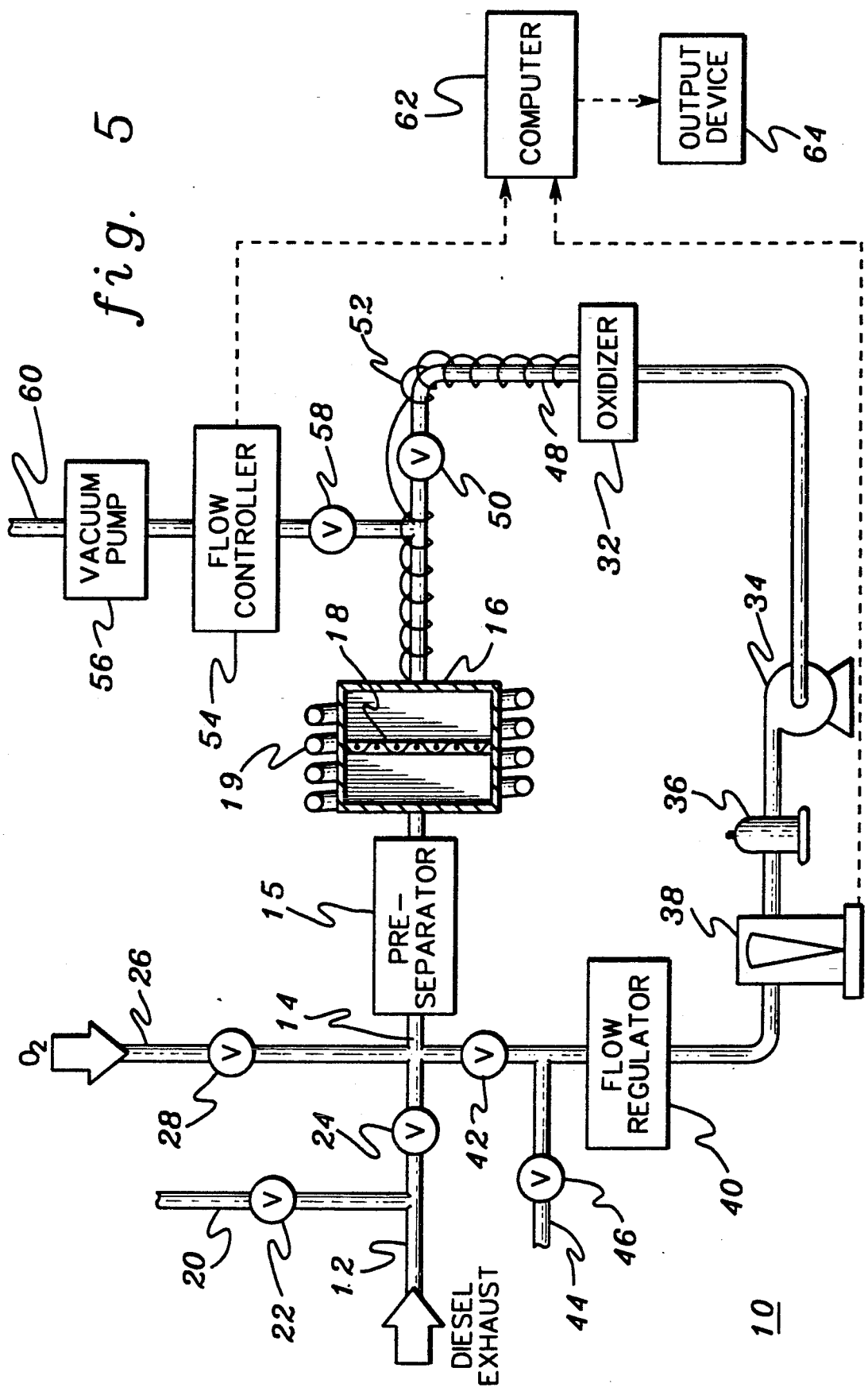
FIG. 5 illustrates an embodiment of the present invention employing a preseperator.

This situation can be alleviated to a certain degree by providing a preseparator 15 upstream of particulate filter 18 (or other equivalent fine particulate collection means) of the measurement apparatus, as shown in FIG. 5. Preseparator 15 serves to remove particulate from the sampled gas stream and/or to sort particulate by size. Diesel particulates are small in size (and aerodynamic cross-section), whereas inorganic particulates are usually produced by fracturing and abrasion processes which tend to produce larger particles. The preseparator allows the fine particulate (typically oxidizable diesel particulate) to pass through to the fine particulate filter 18 in filter chamber 16, while capturing larger size particulate In this way, the fine particulate filter (or equivalent collecting means) avoids clogging with inorganic particulate and can realize an extended lifetime beyond what it would have without a preseparator.

Preseparator 15 can include a heater to facilitate oxidation of any carbon particulate captured by the preseparator, as well as thermal analysis thereof, in the manner earlier described. The heater for the preseparator may comprise a separate oven surrounding the preseparator, or other appropriate heating means. Alternatively, the preseparator can be positioned within the same heatable chamber as the fine particulate filter. Thermal application and/or analyses, as earlier described, can be performed on the preseparator and the fine particle collector either together or separately. This provides a measure of total carbon particulate level or concentration in the gas (both diesel and other) and allows for volatile and non-volatile component measurements, as well as providing an extended life for the fine particulate collector.

Figure 6:
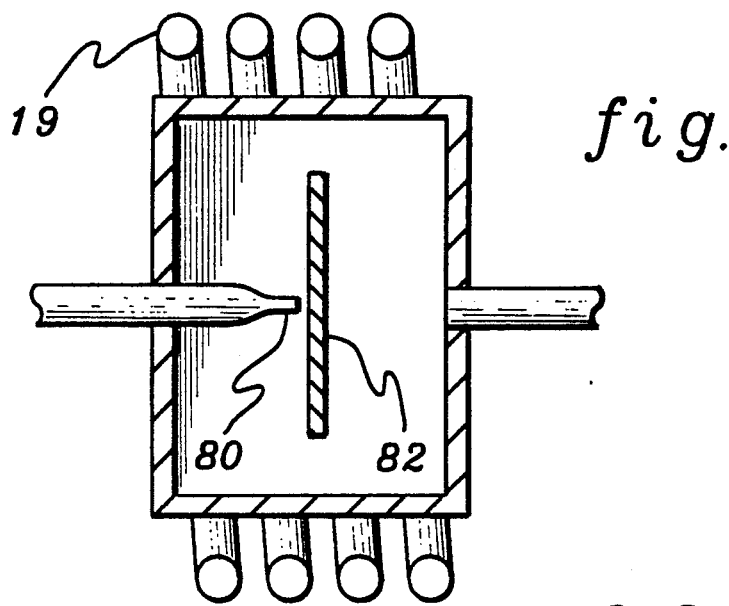
FIG. 6 depicts an impactor type preseparator.
Figure 7:
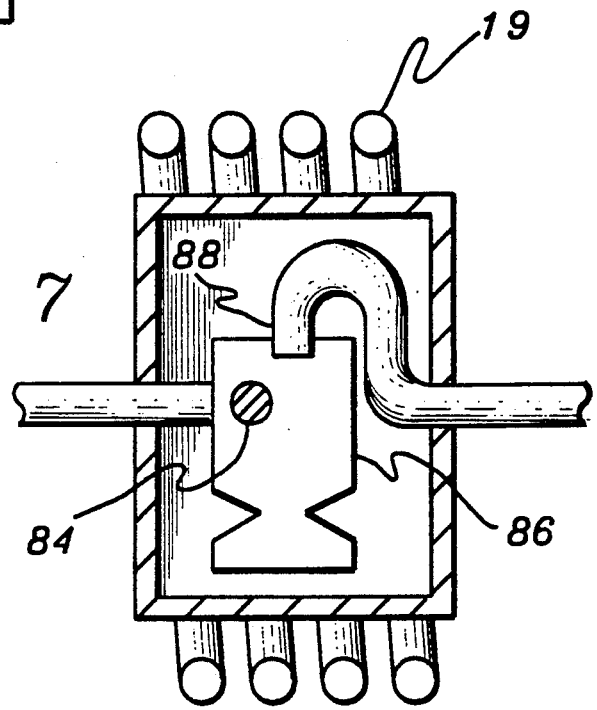
FIG. 7 depicts a cyclone type presepaparator.
Figure 8:
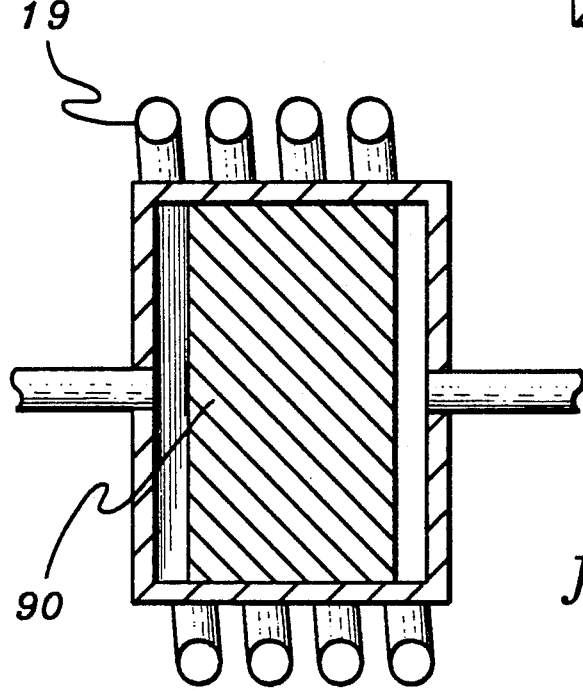
FIG. 8 depicts a depth filter type preseperator.

The preseparator can define a particle size cut such that larger size particles are retained by the preseparator and particles below a certain size are allowed to pass through the preseparator and into the fine particulate collection stage. The preseparator can take various forms as illustrated in FIGS. 6–8. In these figures, each of the preseparators is shown with an optional heater 19 so that carbon in particulate caught in the preseparator can be measured and analyzed as well, if desired. In all cases, the gas stream enters from the viewer's left and exits to the right.

The preseparator of FIG. 6 comprises a classical impactor. In this embodiment, a gas stream is accelerated through orifice 80 such that particles of a specific size, and larger, impact on impaction plate 82. The particle size cut point for this type of impactor depends upon the geometry of the orifice 80 and its separation from impaction plate 82. The characteristics and operation of such impactors are well known in the art. Although a classical impactor is shown in FIG. 6, a virtual impactor, which those skilled in this art will recognize works on similar principles, can be used instead.

FIG. 7 depicts a cyclone type preseparator. In the cyclone preseparator, the gas stream enters tangentially through an opening 84 into a cylindrical body 86. The resulting rotating gas stream separates particles according to their aerodynamic cross-sections so that fine particles are withdrawn at the exit 88 located at the center of the cylindrical body.

Another embodiment of a preseparator suitable for use in the present invention is shown in FIG. 8. This preseparator employs a depth filter 90. The depth filter 90 typically includes less densely packed fibrous material or contains larger openings compared to the fine particulate filter. Thus, the depth filter traps larger sized particulate and is less prone to clogging than the downstream fine particulate filter. If subjected to heating, the depth filter can be made of quartz fibers or the like.

Other structures which perform the desired particulate pre-separation function may be employed as the preseparator 15. Cascaded or multi-stage preseparators may also be employed. The remaining apparatus of FIG. 5 operates in the manner previously described with regard to the embodiment of FIG. 1 to provide an accurate measurement of carbon particulate level or concentration (diesel or otherwise) of sampled gas. Depending upon the nature and composition of the sampled gas, the introduction of a separate oxygen rich gas may be unnecessary to create the desired oxygen rich environment for oxidation and to purge the system. A preseparator may also be advantageously incorporated in other embodiments of the invention, e.g. the system of FIG. 3.

From the foregoing description, it will be apparent that a new method and apparatus for determining carbon particulate level or concentration of diesel exhaust or other sampled gas has been developed which can be advantageously employed, for example, to quickly and accurately determine whether a diesel powered vehicle is operating within emission standards. The measurement instrument can be made as both a research tool and also as a rugged, relatively inexpensive industrial grade device. It can produce particulate measurements in short periods of time with a minimum of labor requirements. Further, it does not require the use of a dilution tunnel and is immune to measurement confounding influences of water vapor in the exhaust or sampled gas. The process of the invention inherently renews the fine particulate filter or collector for future use, thereby avoiding the need to either independently clean or replace the filter or collector after each measurement cycle. Preseparation of inorganic particulates extends the useful life of the fine particulate filter or collector. Further, the invention is susceptible to wide application and can be advantageously employed to monitor carbon particulate level or concentration in various gaseous mixtures and samples. Another advantage is the ready susceptibility of the invention to automated/computer control. The present invention thus represents a significant advance in man's efforts to curb air pollution and maintain air quality.

Although the invention has been described with respect to the embodiments depicted herein, it is evident that the invention may be incorporated into a variety of different embodiments. All such embodiments are intended to be within the scope of the invention as defined by the following claims.

What is claimed is:

1. A method for determining the level or concentration of carbon particulate of sampled gas, comprising the steps of:
   preseparating certain particulate out of the sampled gas;
   collecting carbon particulate from the preseparated sampled gas;
   exposing the collected particulate to oxygen;
   heating the collected particulate to oxidize carbon within the particulate to carbon dioxide;
   measuring the level of resultant carbon dioxide; and
   providing an indication of the level or concentration of carbon particulate based on the measured level of the resultant carbon dioxide.

2. The method of claim 1 wherein the collecting step comprises:
   collecting carbon particulate from a measured amount of sampled gas; and
   wherein said indication providing step comprises determining a level of carbon within the collected particulate from the measured level of resultant carbon dioxide, and calculating carbon particulate concentration by comparing the level of carbon with the measured amount of sampled gas.

3. The method of claim 1 wherein the preseparating step comprises preseparating inorganic particulate out of the sampled gas.

4. The method of claim 1 wherein the preseparating step comprises preseparating particulate of a specified size and greater out of the sampled gas.

5. The method of claim 1 further comprising the step of heating preseparated particulate to facilitate oxidation of any carbon contained therein.

6. The method of claim 1 wherein the collecting step comprises one of (a) passing the sampled gas through an acceleration nozzle and impacting the carbon particulate upon a heatable impaction plate, and (b) passing the sampled gas through a high efficiency, high temperature resistant filter.

7. The method of claim 1 wherein the collected carbon particulate is heated incrementally to evaporate volatile components of the particulate prior to oxidation of non-volatile carbon of said particulate; and further comprising the step of oxidizing the evaporated volatile components into carbon dioxide.

8. The method of claim 1 further comprising the step of converting carbon monoxide which may be produced by partial oxidation of carbon into carbon dioxide.

9. The method of claim 1 wherein said sampled gas comprises diesel exhaust; and further comprising the step of purging residual carbon dioxide gas from the vicinity of the collected carbon particulate with an oxygen rich gas prior to oxidation.

10. Apparatus for providing an indication of the level or concentration of carbon particulate collected and retained by collection means from sampled gas comprising:

means for containing collection means having collected and retained carbon particulate;

means for heating collected particulate within said containing means to oxidize carbon of said particulate;

means for measuring the amount of carbon dioxide produced from oxidation of the carbon of said particulate;

means for establishing a closed recirculating gas measurement loop incorporating said containing means, a separate oxidizer, a pump and said measuring means; and means for providing an indication of the level or concentration of carbon particulate based on the amount of carbon dioxide measured in said closed recirculating gas measurement loop.

11. The apparatus of claim 10 wherein the means for providing an indication comprises:

computer means for calculating particulate concentration from the measured amount of carbon dioxide and a measurement of the amount of a sampled gas from which the particulate is collected.

12. The apparatus of claim 10 further comprising:

means for directing sampled gas at said collection means within said containing means; and means for measuring an amount of sampled gas directed at said collection means.

13. The method of claim 1 wherein the measuring step comprises:

circulating resultant carbon dioxide through a closed measurement loop and measuring the level of resultant carbon dioxide within said loop.

14. A method for determining the level or concentration of carbon particulate of sampled gas, comprising the steps of:

collecting carbon particulate from sampled gas by passing the sampled gas through an acceleration nozzle and impacting the carbon particulate upon a heatable impaction plate;

exposing the collected particulate to oxygen;

heating the collected particulate through the heatable impaction plate to oxidize carbon within the particulate to carbon dioxide;

measuring the level of resultant carbon dioxide; and providing an indication of the level or concentration of carbon particulate based on the measured level of the resultant carbon dioxide.

15. The method of claim 14 wherein the collecting step further comprises collecting carbon particulate from a measured amount of sampled gas; and wherein said indication providing step comprises determining a level of carbon within the collected particulate from the measured level of resultant carbon dioxide, and calculating carbon particulate concentration by comparing the level of carbon with the measured amount of sampled gas.

16. Apparatus for determining the level or concentration of carbon particulate of sampled gas comprising:

means for preseparating certain particulate out of the sampled gas;

means for collecting carbon particulate from the preseparated sampled gas;

means for exposing the collected particulate to oxygen;

means for heating the collected particulate to oxidize carbon within the particulate to carbon dioxide;

means for measuring the level of resultant carbon dioxide; and means for providing an indication of the level or concentration of carbon particulate based on the measured level of the resultant carbon dioxide.

17. The apparatus of claim 16 wherein the preseparating means comprises means for preseparating inorganic particulate out of the sampled gas.

18. The apparatus of claim 16 wherein the preseparating means comprises means for preseparating particulate of a specified size and greater out of the sampled gas.

19. The apparatus of claim 16 further comprising means for heating preseparated particulate to facilitate oxidation of any carbon contained therein.

20. Apparatus for determining the level or concentration of carbon particulate of sampled gas comprising:

means for collecting carbon particulate from sampled gas, said collecting means comprising means for accelerating sampled gas flow and for collecting by impaction upon a directly heatable impaction plate carbon particulate from the accelerated sampled gas flow;

means for exposing the collected particulate to oxygen;

means for heating the collected particulate through said impaction plate to oxidize carbon within the particulate to carbon dioxide;

means for measuring the level of resultant carbon dioxide; and means for providing an indication of the level or concentration of carbon particulate based on the measured level of the resultant carbon dioxide.

21. The apparatus of claim 20 wherein said accelerating means comprises an acceleration nozzle and wherein the heating means comprises means for supplying an electrical current to the impaction plate.

* * * * *